United States Patent [19]
Little et al.

[11] Patent Number: 5,848,115
[45] Date of Patent: Dec. 8, 1998

[54] COMPUTED TOMOGRAPHY METROLOGY

[75] Inventors: Francis H. Little; John C. Janning, both of Cincinnati, Ohio

[73] Assignee: General Electric Company, Cincinnati, Ohio

[21] Appl. No.: 850,673

[22] Filed: May 2, 1997

[51] Int. Cl.[6] .............................. A61B 6/03; G01N 23/04
[52] U.S. Cl. ................ 378/4; 378/901; 382/152
[58] Field of Search ........................ 378/4, 901; 382/141, 382/152; 364/468.17, 468.16

[56] References Cited

U.S. PATENT DOCUMENTS

| | | | |
|---|---|---|---|
| 4,422,177 | 12/1983 | Mastronardi et al. | 378/17 |
| 4,600,998 | 7/1986 | Huet | 364/507 |
| 4,729,098 | 3/1988 | Cline et al. | 345/421 |
| 4,969,110 | 11/1990 | Little et al. | 364/550 |
| 5,027,281 | 6/1991 | Rekow et al. | 364/474.24 |
| 5,119,408 | 6/1992 | Little et al. | 378/4 |
| 5,345,490 | 9/1994 | Finnigan et al. | 378/4 |
| 5,414,647 | 5/1995 | Ebenstein et al. | 364/560 |
| 5,442,572 | 8/1995 | Kiridena et al. | 364/560 |
| 5,452,407 | 9/1995 | Crook | 395/121 |
| 5,559,334 | 9/1996 | Gupta et al. | 250/360.1 |
| 5,621,648 | 4/1997 | Crump | 364/468.19 |

OTHER PUBLICATIONS

Applied Technologies Inc. "Reverse Engineering using X–Ray Tomography" URL http://www.acceltechinc.com/revengineer.html, Nov. 1996.

Imageware "applications how our software is used" URL http://www.iware.com/htmls/uses.html, Sep. 1996.

Imageware "key capabilities what our software can do" URL http://www.iware.com/htmls/key_caps.thml, Sep. 1996.

"Reverse Engineering using X–Ray Tomography", Accelerated Technologies, Inc., 1 page, Internet Document. No Date.

"key capabilities what our software can do", About Imageware, 5 pages, Internet Document. No Date.

"applications how our software is used", Imageware Product Applications, 5 pages, Internet Document. No Date.

"Linear Pushbroom Cameras", R. Hartley and R. Gupta, Presented at the Third European Conference on Computer Vision, Computer Vision–ECCV '94, pp. 555–566, 1994.

"X–Ray Metrology for Quality Assurance", A. Noble, R. Hartley, J. Mundy and J. Farley, Presented at the 1994 International Conference on Robotics and Automation, Proc. IEEE International Conference on Robotics and Automation, pp. 1113–1119, May, 1995.

"Camera Calibration for 2.5–D X–Ray Metrology", R. Gupta, A. Noble, R. Hartley, J. Mundy and A. Schmitz, to be published at the International Conference on Image Processing, to be held Oct., 1995, 4 pages.

*Primary Examiner*—David P. Porta
*Assistant Examiner*—David Vernon Bruce
*Attorney, Agent, or Firm*—Andrew C. Hess; Nathan D. Herkamp

[57] ABSTRACT

The invention is a three-dimensional computed tomography method for inspecting and comparing actual geometry to predetermined geometry of an object. The method includes the following steps: A) three-dimensionally scanning the object using computed tomography to produce multiple slices of actual geometrical data of the object; B) processing the multiple slices of actual geometrical data into actual boundary data which defines internal and external boundaries of the object; and C) producing actual point cloud data from the actual boundary data. The method further includes comparing the actual point cloud data to object geometry predetermined data. The comparing may include outputting an image comparing the point cloud data to the predetermined data and the image may represent the geometry of non-conformance between the point cloud data and the predetermined data. The image may be rotated to present the non-conformance from different viewpoints around the feature.

20 Claims, 7 Drawing Sheets

COMPUTED TOMOGRAPHY METROLOGY

BACKGROUND OF THE INVENTION

1. Field of the Invention

The present invention relates generally to computed tomography (CT) and computer-aided design (CAD) and, more particularly, to using computed tomography (CT) to generate three-dimensional actual object point cloud data and compare it to predetermined object data, such as computer-aided design (CAD) data, particularly, for the purpose of non-destructive part inspection.

2. Discussion of the Background Art

Manufacturing of parts having interior cavities and passageways is very important to many industries such as the auto and gas turbine engine industries. Parts, such as casings, are often made from castings designed with a number of internal cavities and passageways which are used for purposes such as cooling and lubrication. Often such manufactured parts may not be the same as the design definition to which it is being manufactured. This may be because of manufacturing tolerances in the system, material shrinkage, or part warpage caused by residual stresses. Thus, when analysis is performed on the designed part, the physical part dimensions may be sufficiently different that the analysis is suspect. Such discrepancies between the manufactured part definition and the design or predetermined part definition and discrepancies must be determined and examined before the part can be accepted. Therefore, methods are needed for part verifying as regards the accuracy of a part geometry with respect to a predetermined part definition or design geometry.

The typical method used to test and examine such parts involves the use of destructive techniques in which the part is cut up and examined. This is a very costly and time consuming technique. In the case of complex part designs these techniques may not be sufficiently accurate for the parts designed purpose.

The use of non-destructive topographical evaluation of the accuracy of manufactured parts with complex external geometries has been addressed in the prior art. One group of such patents which disclose the use of computer-generated models related to fabricating objects having unique geometries, such as a dental prosthesis include U.S. Pat. Nos. 5,257,203, 5,121,334 and 5,121,333 of Riley et al., 5,184,306 and 5,128,870 of Erdman et al., and 5,027,281 of Rekow et al. Each of these cited patents disclose steps involved with creating a computer model for use with a milling machine. U.S. Pat. No. 5,442,572, entitled, Method and System for Comparing Free-form Geometries Using High Density Point Data Models, by Kiridena et al., discloses a method for verifying the accuracy of a part geometry with respect to a master geometry ending with the step of displaying an image on an output device based on the differential distance data between the part and master geometry. The method discloses the use of laser scanning for generating the part geometry. The image represents the non-conformance between the master and the part and is used to verify the accuracy of the geometry of the part with respect to the geometry of the master. These references disclose external topographical scanning but none of the references, however, disclose methods for verifying conformance of a manufactured part having internal cavities and/or passages to the computer model or for the use of scanning techniques which can be used with parts having the internal cavities and passages. None of the references disclose methods for providing an image representing the non-conformance of internal passages, cavities, and features between the predetermined part and the actual part as such images may be used to verify the accuracy of the geometry of the part with respect to the geometry of the predetermined part.

The present invention addresses the problem of providing a method for comparing three-dimensional images of actual and predetermined geometric data of objects having internal hollow features such as cavities and passages, displaying these internal features, and displaying three-dimensional representations of geometry of non-conformance between the actual and predetermined geometric data of these internal features. CT systems, methods, and apparatus are well known in the art for inspecting large objects such as a gas turbine engine component, rocket engine component, or the like. They typically include a source of radiation and an associated detector both of which can be moved, relative to an object under inspection for purposes of reconstructing a cross-sectional area or slice through the object at a selected location on the object by means of penetrating the object with radiation and detecting the attenuation of the radiation caused by the object on an opposite side of the object from the radiation source. One x-ray inspection method and apparatus using Computed Tomography (CT) for which this invention was designed to be used with is explained in more detail in U.S. Pat. No. 5,119,408 which is incorporated herein by reference.

SUMMARY OF THE INVENTION

The invention provides a method for comparing actual geometry to predetermined geometry of an object, the method includes the following steps: A) three-dimensionally scanning the object using computed tomography (CT) to produce multiple slices of actual geometrical data of the object; B) processing the multiple slices of actual geometrical data into actual boundary data which defines internal and external boundaries of the object; and C) producing actual point cloud data from the actual boundary data. The method further includes comparing the actual point cloud data to object geometry predetermined data. The comparing preferably includes registering the point cloud data to coordinates of the predetermined data and in one embodiment the predetermined data is computer aided design (CAD) data and registration is made to CAD coordinates of the predetermined data. The comparing may include outputting an image comparing the point cloud data to the predetermined data and the image may be displayed on a computer monitor in color. The image may represent the geometry of non-conformance between the point cloud data and the predetermined data. The image may be an image of an interior feature of the object and the image may represent the geometry of non-conformance between the point cloud data and the predetermined data. The displaying may include displaying a plurality of pixels representing the geometry of non-conformance between the point cloud data and the predetermined data of the interior feature of the object. The method may be used to display non-conformance of an interior feature or features of the object such as a core. Another embodiment of the invention uses the 3D CT metrology method of the present invention to scan cooling holes of an air cooled airfoil such as of a turbine vane or blade to produce a point cloud of the cooling hole, surface fit a predetermined shape of the cooling hole to the point cloud of the cooling hole, calculate a actual geometric definition to the predetermined geometric definition.

ADVANTAGES OF THE INVENTION

The present invention provides time and cost saving advantages over previous methods of inspection nonconformance of internal passages, cavities, and features between a predetermined part and an actual part to verify the accuracy of the geometry of the part with respect to the geometry of the predetermined part. The present invention is particularly advantageous because it provides a three-dimensional method for making this comparison. Another advantage of the present invention is that it allows an accurate non-destructive evaluation of parts during manufacturing as well as developmental processes and can provide a great deal of savings in both time and money over previous destructive methods. The present invention also has the ability to more accurately and quickly pinpoint which areas of the part should be further examined.

BRIEF DESCRIPTION OF THE DRAWINGS

The novel features believed characteristic of the present invention are set forth and differentiated in the claims. The invention, together with further objects and advantages thereof, is more particularly described in conjunction with the accompanying drawings in which:

DETAILED DESCRIPTION

The present invention provides a method for comparing three-dimensional images of actual CT scanned data and predetermined geometric data of objects having internal hollow features such as cavities and passages, displaying these features, and displaying three-dimensional representations of the geometry of non-conformance between the actual CT scanned data and predetermined geometric data. The invention is particularly useful for quality control purposes to quickly, efficiently, and inexpensively perform non-destructive testing on developmental and production parts such as cast turbine vanes and blades with cooling holes and cast casings such as transmission cases and fuel control housings.

Figure 1:
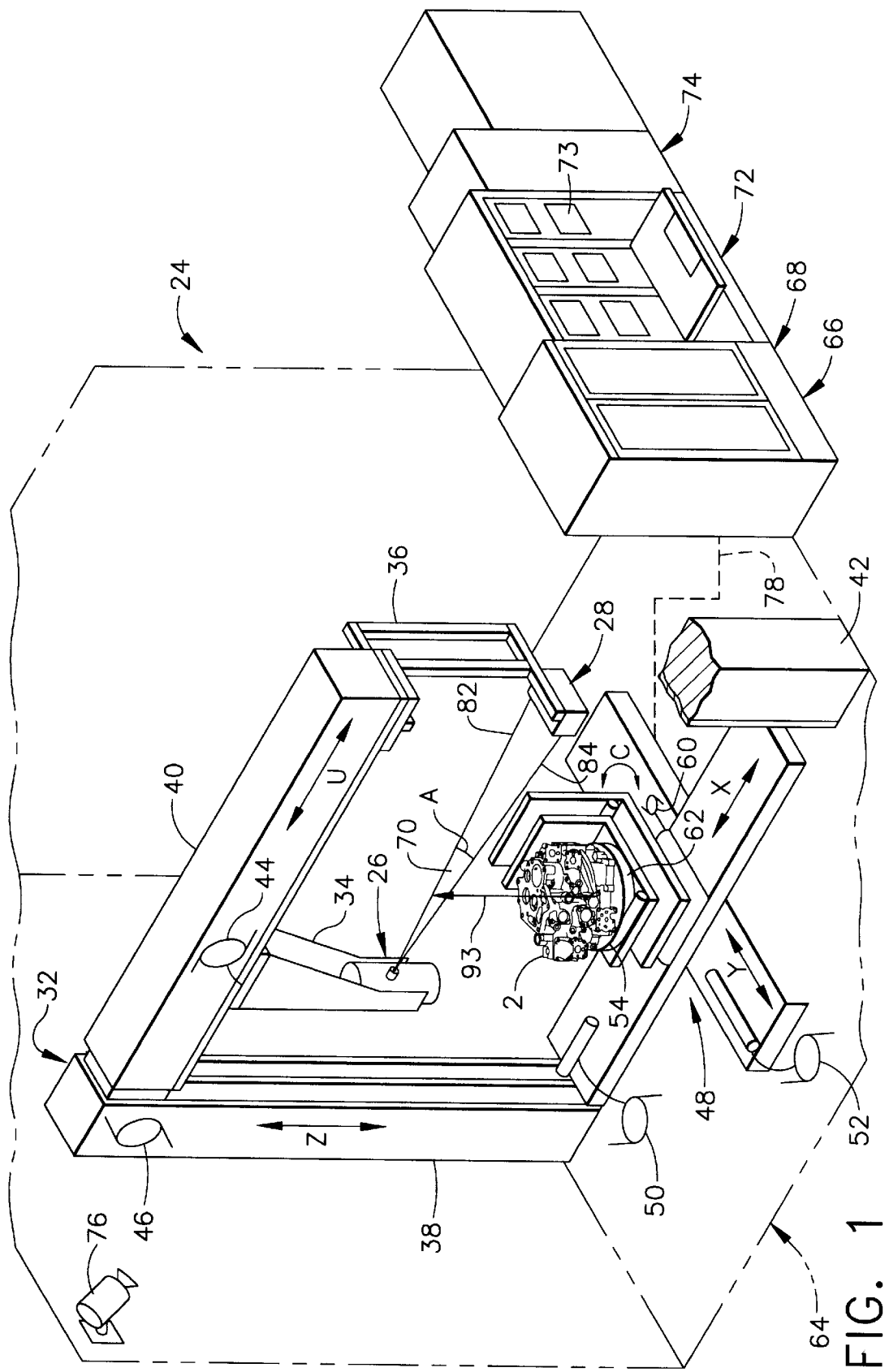
FIG. 1 is a perspective view of fuel control casing mounted in a CT X-ray inspection system illustrating a method of comparing three-dimensionally CT scanned data to predetermined CAD data in accordance with a first exemplary method of the present invention.
Figure 2:
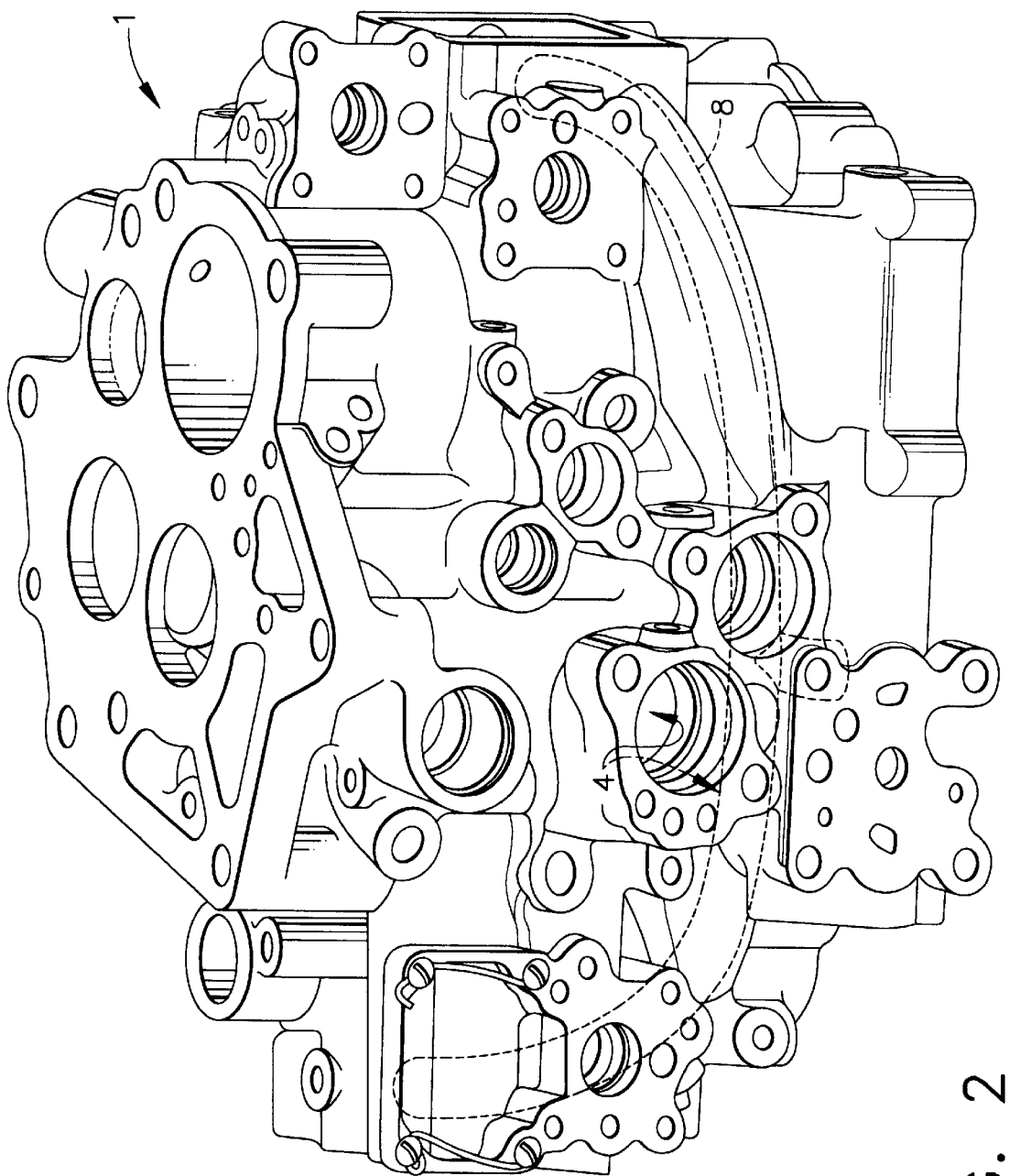
FIG. 2 is an enlarged perspective view of the fuel control casing in FIG. 1 illustrating an internal core or passage of the casing.
Figure 3:
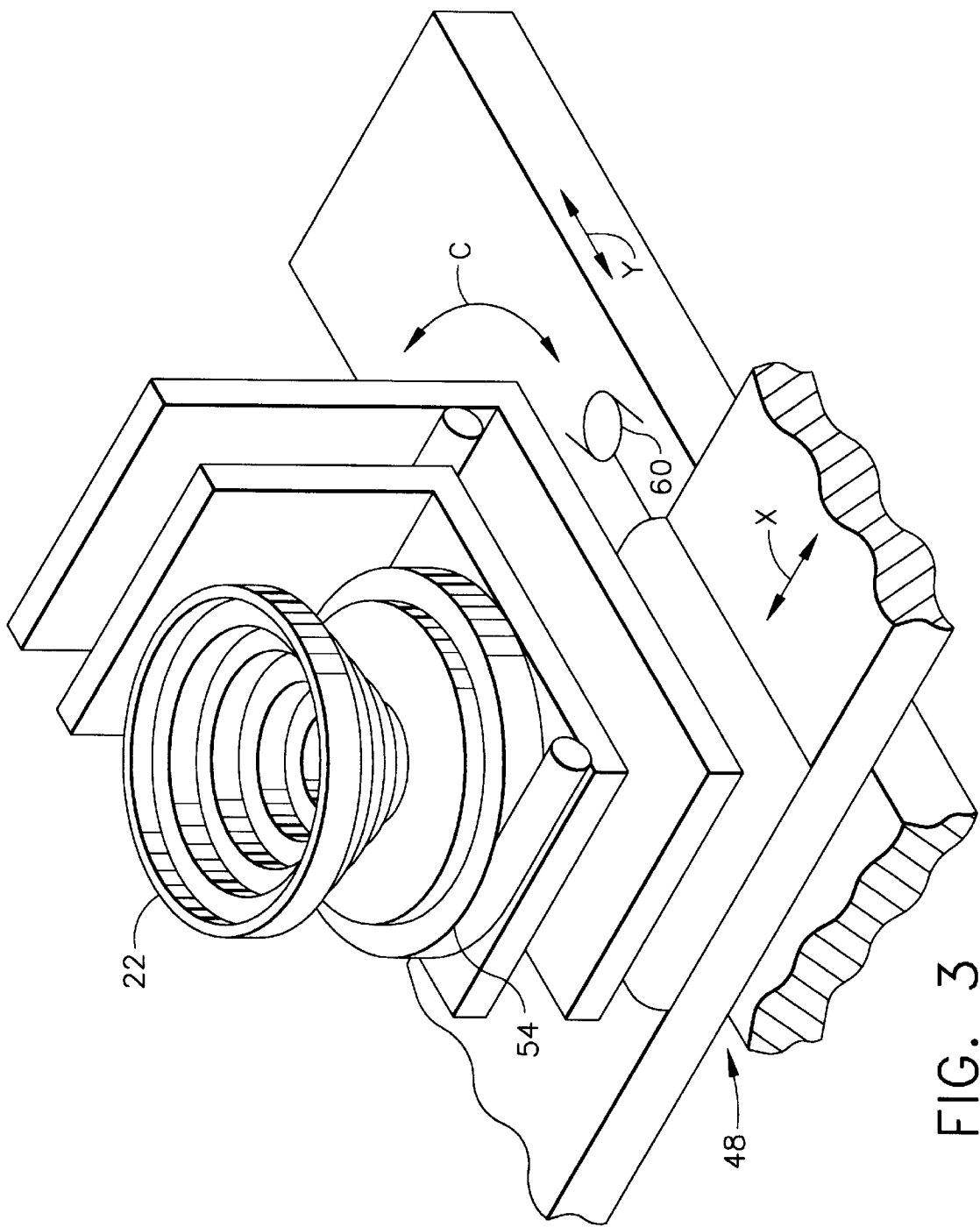
FIG. 3 is a perspective view of a CT X-ray calibration standard used to calibrate the CT X-ray inspection system illustrated in FIG. 1.

Referring now to the drawings, there is diagrammatically illustrated in FIG. 1 a fuel control casing 2 mounted in a fixture 62 of a suitable x-ray computed tomography scanning system, hereinafter referred to as CT system 24, such as an industrial computed tomography system as described in U.S. Pat. No. 5,119,408. Suitable x-ray computed tomography scanning systems are well known in the art, an example being a GE Aircraft Engines' Industrial Computed Tomography System. The casing 2 (which serves as an exemplary object to explain the method of the present invention) has multiple internal hollow features such as a passages 4, illustrated in greater detail in FIG. 2, which are generically referred to as internal cores and includes an exemplary a forked fluid passage 8. The purpose of the present invention is to three-dimensionally compare the geometry of actual cores to the geometry of the designed or predetermined internal features or cores. The predetermined data is preferably stored, as in this exemplary embodiment of the invention, as CAD data. The method begins by calibrating the CT system 24 using a calibration standard 22 illustrated in FIG. 3 mounted in the fixture 62 in FIG. 1.

Referring again to FIG. 1, the CT system 24, described in fuller detail in the above referenced U.S. Pat. No. 5,119,408, includes an x-ray source 26, such as a Philips MG model 450 420 kV high stability constant potential x-ray system, a Lintron 2 MeV source or the like, and an x-ray detector 28 such as a Xenon gas-type detector, solid state scintillator or the like. Higher resolutions are possible by using known multiple sampling schemes. Detector elements (not shown) are preferably spaced in the linear array on centers of about 0.005 inches to about 0.01 inches apart to provide the high resolution.

X-ray source 26 and detector 28 are mounted to a gantry-type structure 32 by support members 34 and 36, respectively. Gantry structure 32 includes at least one vertical member 38 and a horizontal member 40 extending from vertical member 38. A second vertical member 42, partially shown in FIG. 2, may be provided for additional support. Support member 34 and detector 28 may be moved linearly along horizontal member 40 by a servomotor 44 in the directions indicated by axis U. Detector 28 and its associated support member 36 may be stationary or support 36 may be interconnected to source support members 34 to permit coordinated motion of both x-ray source 26 and detector 28. Horizontal member 40 may also be moved along axis Z by servomotor 46 to control the elevation of x-ray source 26 and detector 28.

A part manipulator 48 is located at the base of gantry structure 32 for controlling the motion of the object 1 under inspection relative to the x-ray source 26 and detector 28. Part manipulator 48 preferably includes two linear axes of motion, indicated by directional arrows X and Y, and a rotary axis of motion indicated by arrows C. Motion along linear axes X and Y is controlled by known techniques such as servomotors and gear combinations 50 and 52. Rotary platforms 54 permits rotary motion about rotary axis 93 as indicated by rotational direction arrow C. Servomotor 60 controls rotary motion of platform 54. Platform 54 includes a fixture 62 for mounting the object 1 to be examined.

CT system 24 is housed in a system enclosure 64 and a system computer 66 is provided to control operation of CT system 24. A data acquisition system (DAS) 68 receives electrical signals from detector 28 which correspond to the attenuated x-ray beam 70 that passes through a part under inspection and converts the low voltage analog detector change signals received to a quantified digital values which are stored and later recalled for multiplexing with other received and converted signals to reconstruct a cross-sectional image of the object being examined to produce slice data. These values are used in the exemplary method of the present application.

Communications between CT system 24 and the combination of computer 66, DAS 68 and operator console 72 is accomplished through a plurality of communications links 78 indicated by a broken line. The present invention uses the computer to automatically do the scanning. The electrical signals, corresponding to the attenuated x-ray beam that passes through the object, are also transmitted from detector 28 to computer 66 and DAS 68 by one of communications links 78.

In accordance with the present invention, after the CT system 24 has been calibrated, the casing 2 is mounted in the same fixture 62 which held the calibration standard 22 during calibration and moved by manipulator 48 within a fan angle A of x-ray beam 70 which is a fan beam. The casing 2 is three-dimensionally scanned within the x-ray beam 70 by continuously rotating the casing within the boundaries 82 and 84 of the fan beam which may have a fan beam angle A between about 5 and about 30 degrees. After the x-ray beam 70 is generated by x-ray source 26, the object is rotated 180 degrees plus the scan fan angle A around the rotary axis 93 to get a full 360 degrees CT scan. The attenuated x-ray beam that passes through the casing 2 during rotation is collected by elements of detector 28. Detector 28 generates a multiplicity of electrical signals responsive to the collected attenuated x-ray beam which are transmitted to computer 66 and DAS 68 by communications links 78. Rotation is performed at the incremental heights along the Z axis with data collected at each height used to provide slice data in a suitable manner as is well known and documented in the art.

After reconstructing an image of one slice through the object, the next slice or image through the object is taken at a different incremental elevation by moving gantry horizontal member 40 along the Z axis. The entire object is three-dimensionally scanned in this manner by incrementally elevating the horizontal member 40 along the Z axis until the entire casing 2 has been three-dimensionally scanned. The slice data 100 representing the images of the slices at different elevations through object are then processed in accordance with the method of the present invention as illustrated in a flow chart in FIG. 4.

Figure 4:
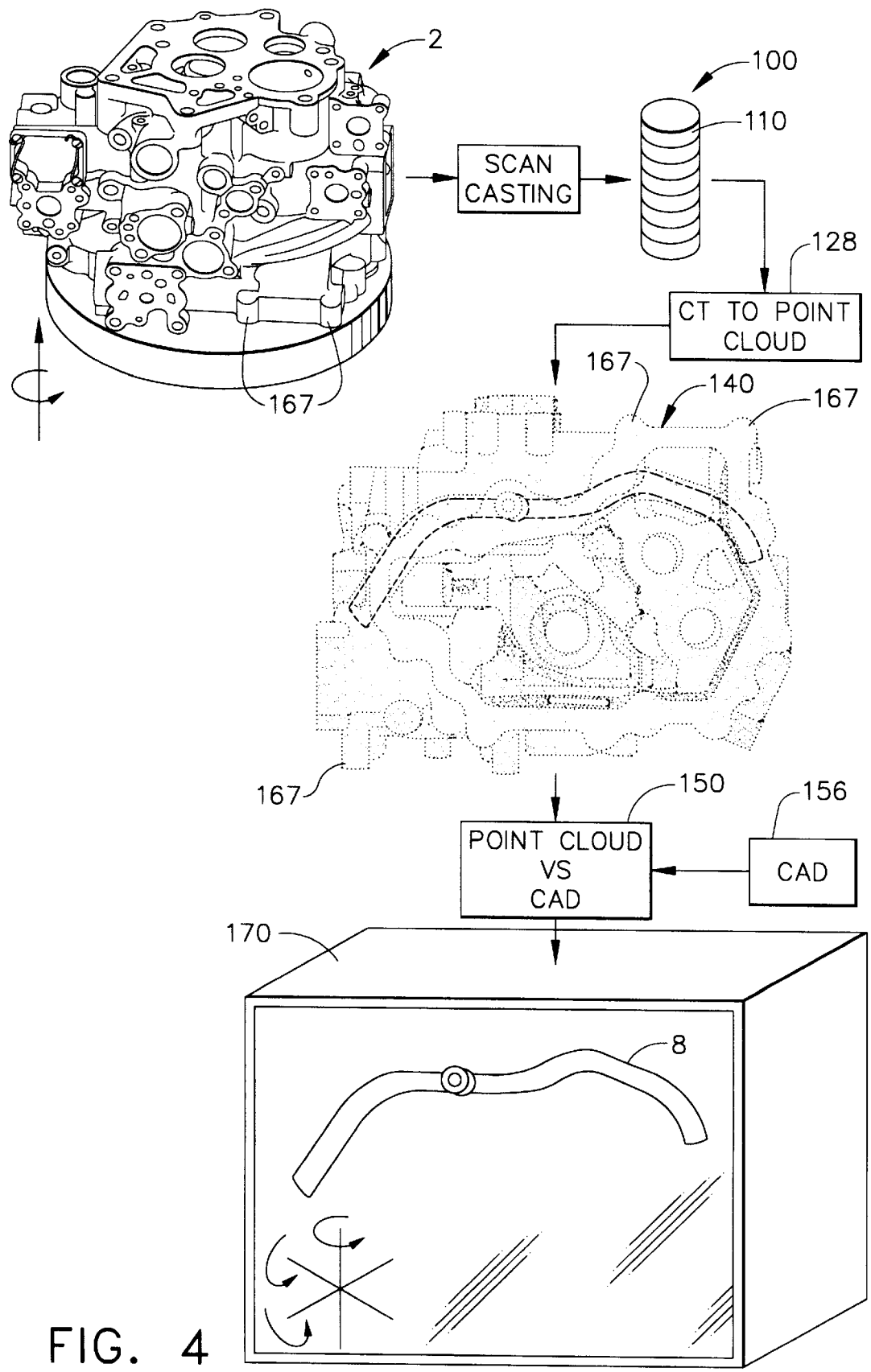
FIG. 4 is a diagrammatic flow chart illustrating the method of three-dimensionally scanning an object and comparing the scanned actual data to predetermined CAD data of a forked fluid passage in the fuel control casing in FIG. 1 in accordance with a first exemplary method of the present invention.

Briefly, the flow chart of FIG. 4 illustrates the scanning of the casing 2 including the forked fluid passage 8 within using the CT system 24 to three-dimensionally x-ray scan the casing to produce two-dimensional images in the form of thin slice data 100 through the cross-section of the object. The scanning process is carried out so as to produce a great many contiguous cross-sectional slices 110 in the slice data 100. The scanning is done 360 degrees or 180 degrees plus the scan fan angle A around the object's rotary axis 93 through the casing 2 and at different heights along the axis 93 in the Z direction to produce an ensemble of slices 110 about 0.005 inches apart along the rotary axis 93. The raw scanned data is density data which is then converted into point cloud data 140 as represented by an image of the point cloud data in the figures. The point cloud data 140 is derived from the raw scanned data or slice data 100 by using an edge detection computer code 128 that define edges of the internal and external features of the casing 2. This is particularly useful for internal features inside the casing such as those of the forked fluid passage 8. Computerized edge detection techniques are known in the art such as those described in U.S. Pat. No. 5,345,490. Various suitable computerized edge detection methods, processes, and computer codes and routines are well known in the art, documented, and commercially available. The use of computer tomography to three-dimensionally scan an object, produce slice data, and construct finite element and discrete solid models are known in the art.

The point cloud data 140 is calculated very closely together, about every 0.005 inches such that actual surfaces of the interior features, such as the internal core of forked fluid passage 8, are well defined. Some or all of the actual point data is preferably assembled in what is referred to as the point cloud data 140 defining the surfaces of some or all of the internal and external features of the object and loaded into a surfacing computer program 150 or code.

Within the surfacer program 150 the point cloud data is then compared to previously stored or predetermined data defining the object and the object's internal and external features and their surfaces. The predetermined data is preferably stored as a CAD data 156 file and if so desired is converted into a standardized CAD data file format such as IGES. The predetermined CAD data 156 and the point cloud data 140 are loaded into the computer surfacing program 150 (or a surfacing routine) such as Surfacer by Imageware, Inc. of Ann Arbor, Mich.

The next step in comparing the predetermined CAD data 156 and the point cloud data 140 is registration of one set of data to the other set of data. The present invention preferably sets the point cloud data to the coordinates of the predetermined data and registration is made to CAD coordinates of the predetermined data. The Surfacer computer code includes registration techniques which precisely align point data from multiple scans to re-assemble them or align point data to CAD geometry for inspection purposes such as those of the present invention. Registration features 167, typically external features, in the point cloud data and the CAD data are identified to the Surfacer program which then does a best fit and registration of the point cloud data to the CAD data.

Surfacer provides point processing and curve and surface fitting capabilities used to manipulate and three-dimensionally analyze the geometry of the actual casing 2 as represented by the point cloud data 140 for accuracy and quality control purposes. This is done by three-dimensionally comparing the point cloud data 140 the to predetermined CAD data 156. The method of the present invention uses the Surfacer or other surfacing routine to display individual features of the actual or point cloud data 156 such as that of the forked fluid passage 8 as illustrated output on a computer monitor 170 in FIG. 4.

Figure 5:
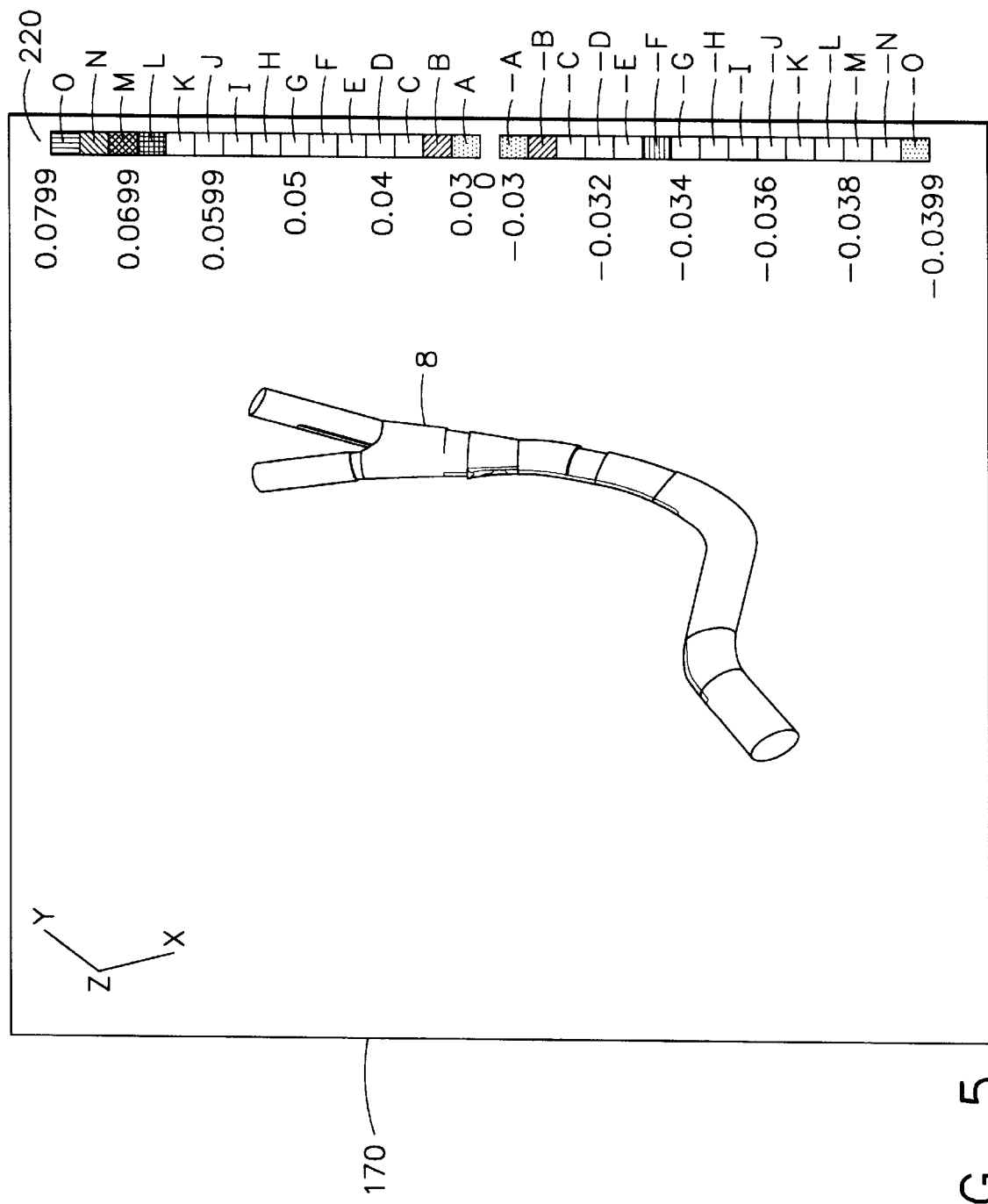
FIG. 5 is a perspective view of the monitor in FIG. 4 illustrating a three-dimensional display of non-conformance of scanned actual data to predetermined CAD data of the forked fluid passage in accordance with a first exemplary method of the present invention.
Figure 6:
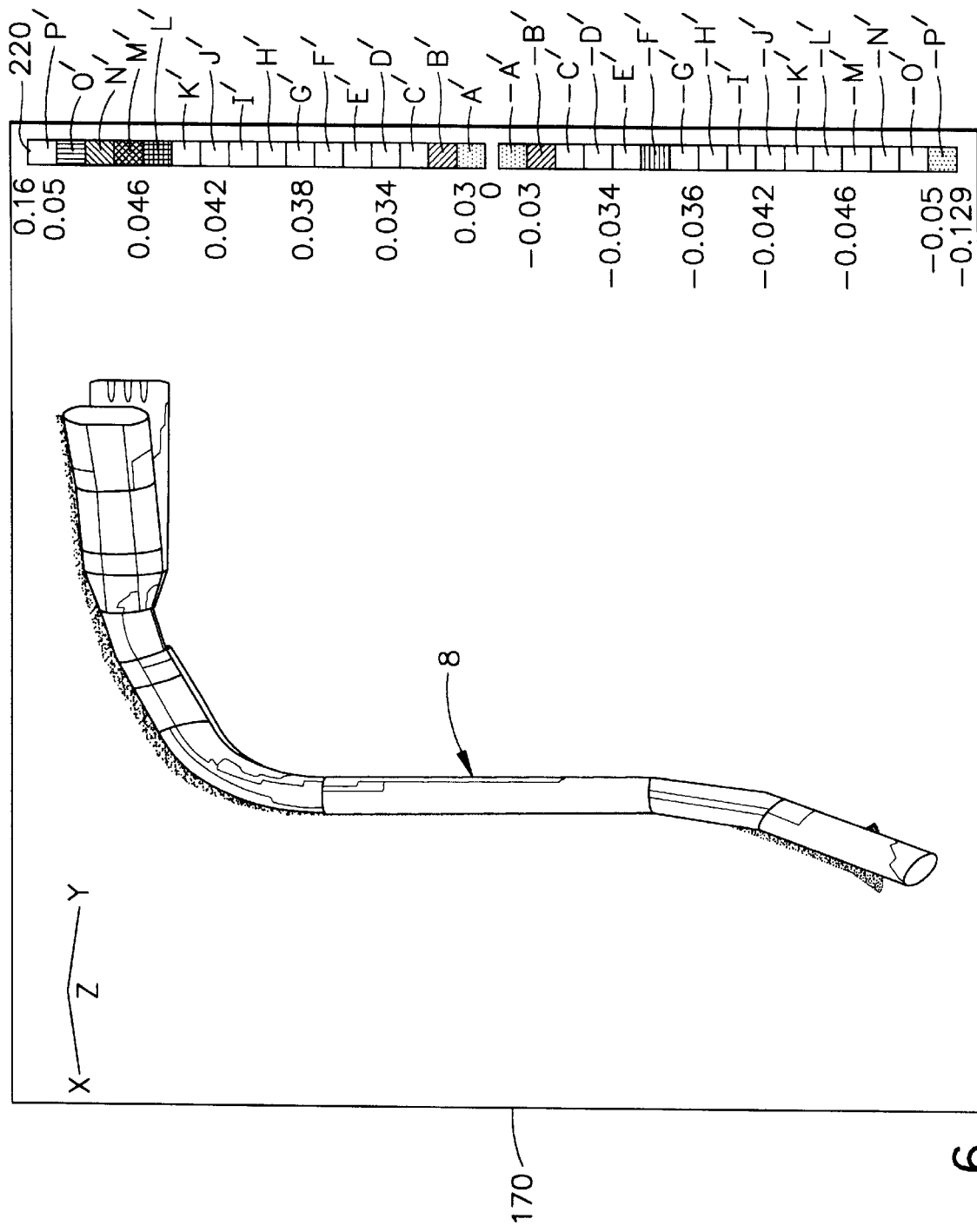
FIG. 6 is a perspective view of the monitor in FIG. 4 illustrating a three-dimensional display of non-conformance of scanned actual data to predetermined CAD data of the forked fluid passage in taken from a different viewpoint from that in FIG. 5.

The method is particularly useful for quality control for which it may be used to check the accuracy of the actual part geometry to a design part geometry such as by comparing the actual point cloud data 140 to predetermined CAD data 156 of internal features of the part such as the forked fluid passage 8. Surfacing includes a means for comparing the digitized point cloud data from the actual part to the predetermined data from the CAD model geometry with visual display and Surfacer has full reporting capabilities of variances between the actual data and the predetermined data. Furthermore, the variances may be observed three-dimensionally by viewing the comparison from different locations and view points around the part as shown in FIGS. 5 and 6 which illustrate variances or non-conformance between the actual and predetermined data in color, where a legend 220 includes a scale having different colors –O through O in FIG. 5 and –P' through P' in FIG. 6 which represent ranges of variance of the forked fluid passage 8. By viewing the variances three-dimensionally the observer or inspector can get a much more accurate appraisal of the quality or conformance of the part. The quality control assessment of non-conformance may be done automatically or by operator vision. Note that the total range of variance may differ from viewpoint to viewpoint as illustrated by the differences in counterpart numerical ranges NR and NR' in FIGS. 5 and 6, respectively. This further points out the advantage of the present data as opposed to merely assembling slice data either CT scanned or cut as previously done in the art.

Figure 7:
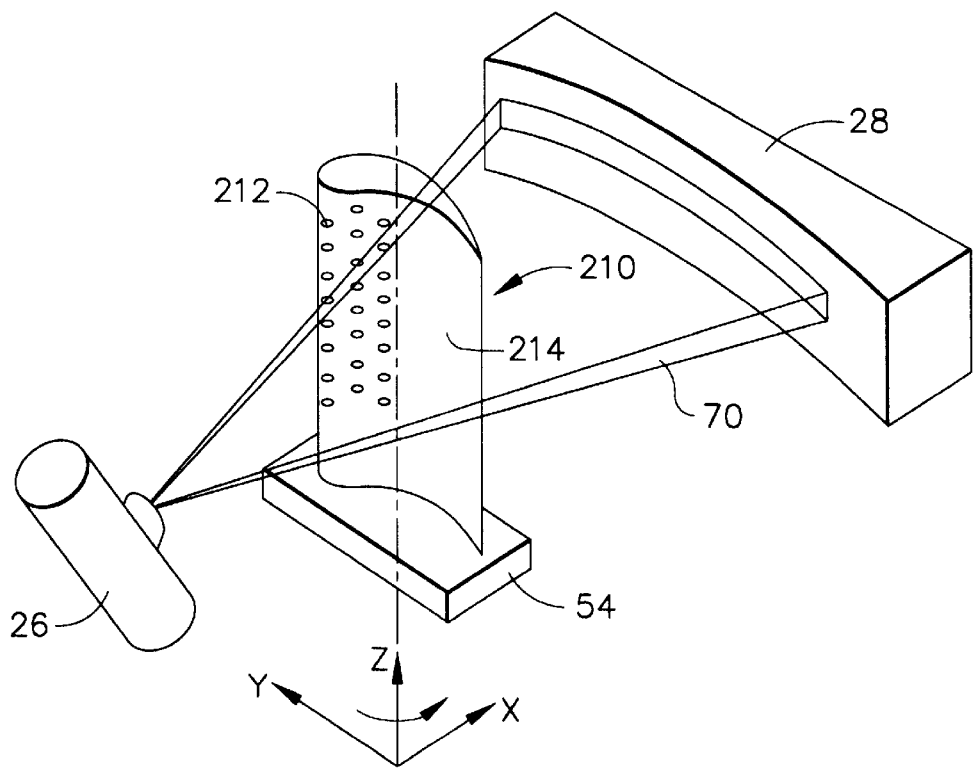
FIG. 7 is a perspective view of cooled turbine blade being three-dimensionally CT scanned illustrating a second exemplary application of the method of the present invention.
Figure 8:
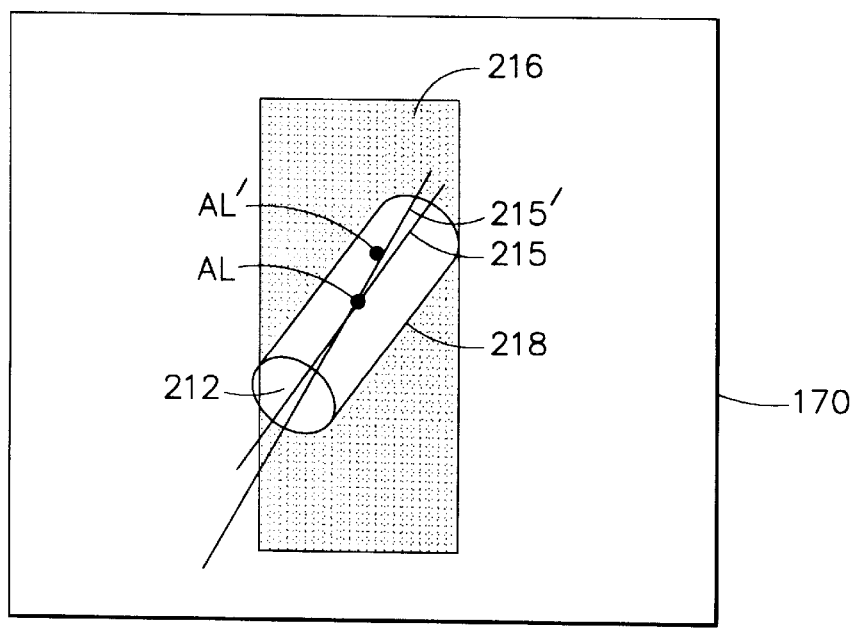
FIG. 8 is a perspective view of illustrating the method of comparing actual point cloud derived from the scanning illustrated in FIG. 7 to predetermined CAD data of a cooling hole of the turbine blade in FIG. 7.

FIG. 7 illustrates a second exemplary embodiment of the present invention which may be applied to the examination and/or inspection of a cooled turbine blade 210 having cooling holes 212 disposed though a wall 214 of the turbine blade. The present invention may also be used to check accuracy of actual centerlines 215 of the cooling holes 212 as to both the location and orientation of the actual centerlines. The 3D CT metrology method of the present invention scans the turbine blade 210 with an x-ray beam 70 from the x-ray source 26 and the x-ray detector 28 to get slice data as disclosed above and then provide blade point cloud data 216 to the Surfacer program. Surfacer is used to surface fit a predetermined shape 218, a cylindrical shape in the embodiment illustrated in FIG. 8, of the cooling holes 212 to the blade point cloud data 216 of the cooling hole. Surfacer is the used to calculate actual geometric data or geometric definitions of the actual features such as the cooling holes 212 using the actual blade point cloud data 216 corresponding to the predetermined shape 218. One geometric definition of the predetermined shape, which in this case is a cylindrical hole, includes the actual centerline 215 and a corresponding actual centerline location AL. Surfacer then visually compares the actual centerline 215, including its orientation in space, and centerline location AL to predetermined geometric definitions of predetermined centerline 215', including its orientation in space, and centerline location AL' previously stored in CAD format in Surfacer. Surfacer may then be used for quality control inspection for non-conformance by automatic or by operator visual means. The picture in FIG. 8 may be rotated for views from different viewpoints to three-dimensionally inspect the actual cooling hole 212.

The foregoing descriptive embodiments of the invention have been presented for the purpose of describing and illustrating the invention. It is not intended to be exhaustive or to limit the invention to the precise form disclosed, and obviously many modifications and variations are possible in light of the above teachings. While the preferred embodiment of the invention has been described fully in order to explain its principles, it is understood that various modifications or alterations may be made to the preferred embodiment without departing from the scope of the invention as set forth in the appended claims.

What is claimed is:

1. A method for comparing actual geometry to predetermined geometry of an object, the method comprising:

three-dimensionally scanning the object using computed tomography (CT) to produce multiple slices of actual geometrical data of the object;

processing said multiple slices of actual geometrical data into actual boundary data which defines internal and external actual boundaries of the object and features of the object; and producing point cloud data from the actual boundary data.

2. The method of claim 1 further comprising comparing the point cloud data to object geometry predetermined data.

3. The method of claim 2 wherein said comparing of the point cloud data to the predetermined data includes registrating the point cloud data to coordinates of the predetermined data.

4. The method of claim 3 wherein the predetermined data is computer aided design (CAD) data and registration is made to CAD coordinates of the predetermined data.

5. The method of claim 3 wherein said comparing includes outputting an image comparing the point cloud data to the predetermined data.

6. The method of claim 5 wherein said outputting includes producing an image representing the geometry of non-conformance between the point cloud data and the predetermined data.

7. The method of claim 6 wherein said outputting an image includes displaying the image on a color computer monitor.

8. The method of claim 7 wherein said displaying the image includes displaying a plurality of pixels representing the geometry of non-conformance between the point cloud data and the predetermined data.

9. The method of claim 5 wherein the image is an image of an interior feature of the object.

10. The method of claim 9 wherein said outputting includes producing an image representing the geometry of non-conformance between the point cloud data and the predetermined data.

11. The method of claim 10 wherein said outputting an image includes displaying the image on a color computer monitor.

12. The method of claim 11 wherein said displaying the image includes displaying a plurality of pixels representing the geometry of non-conformance between the point cloud data and the predetermined data of the interior feature of the object.

13. The method of claim 3 further comprising comparing an actual geometric definition to a predetermined geometric definition of a feature of the object.

14. The method of claim 13 wherein said comparing the actual geometric definition to the predetermined geometric definition of the feature of the object comprises:

generating a curve fitted geometry of the point cloud data representing the feature, calculating the actual geometric definition from the curve fitted geometry, and comparing the actual geometric definition to the predetermined geometric definition.

15. A method for comparing actual geometry to predetermined geometry of an object, the method comprising:

three-dimensionally scanning the object using computed tomography (CT) to produce multiple slices of actual geometrical data of the object;

processing said multiple slices of actual geometrical data into actual boundary data which defines internal and external actual boundaries of the object and features of the object;

producing point cloud data from the actual boundary data;

comparing the point cloud data to object geometry predetermined data wherein said comparing of the point cloud data to the predetermined data includes registrating the point cloud data to coordinates of the predetermined data and outputting an image comparing the point cloud data to the predetermined data wherein the image is an image of an interior feature of the object;

said outputting includes producing an image representing the geometry of non-conformance between the point cloud data and the predetermined data and displaying the image on a color computer monitor by displaying a plurality of pixels representing the geometry of nonconformance between the point cloud data and the predetermined data of the interior feature of the object which is a core.

16. A method for comparing actual geometry to predetermined geometry of an object, the method comprising:

three-dimensionally scanning the object using computed tomography (CT) to produce multiple slices of actual geometrical data of the object;

processing said multiple slices of actual geometrical data into actual boundary data which defines internal and external actual boundaries of the object and features of the object;

producing point cloud data from the actual boundary data;

comparing the point cloud data to object geometry predetermined data wherein said comparing of the point cloud data to the predetermined data includes registrating the point cloud data to coordinates of the predetermined data; and comparing an actual geometric definition to a predetermined geometric definition of a feature of the object by generating a curve fitted geometry of the point cloud data representing the feature, calculating the actual geometric definition from the curve fitted geometry, and comparing the actual geometric definition to the predetermined geometric definition wherein the object is a cooled turbine airfoil having at least one plurality of turbine cooling holes extending from an internal cavity through an outer wall of the airfoil.

17. The method of claim 16 wherein said comparing of the point cloud data to the predetermined data further comprises generating a curve fitted geometry of the cooling holes by curve fitting a predetermined shape of each of the holes to the point cloud data representing the holes.

18. The method of claim 17 wherein said each of said holes is axisymmetric having a predetermined axis and said predetermined axis is compared to an actual axis calculated from geometry of the curve fitted geometry.

19. The method of claim 18 wherein said comparing the actual geometric definition to the predetermined geometric definition includes displaying images of said predetermined axis and said actual axis on a computer monitor.

20. The method of claim 19 wherein said comparing the actual geometric definition to the predetermined geometric definition further includes rotating the displayed images of the predetermined axis and the actual axis on a computer monitor to view nonconformance between the predetermined axis and the actual axis from different viewpoints around the cooling hole.

* * * * *